(12) United States Patent
Gabbay

(10) Patent No.: US 6,264,691 B1
(45) Date of Patent: Jul. 24, 2001

(54) APPARATUS AND METHOD FOR SUPPORTING A HEART VALVE

(76) Inventor: Shlomo Gabbay, #1 Randall Dr., Short Hills, NJ (US) 07078

(*) Notice: Subject to any disclaimer, the term of this patent is extended or adjusted under 35 U.S.C. 154(b) by 0 days.

(21) Appl. No.: 09/298,493

(22) Filed: Apr. 23, 1999

(51) Int. Cl.⁷ .................................................. A61F 2/24
(52) U.S. Cl. .................. 623/2.14; 623/2.18; 623/2.38; 623/904; 600/37
(58) Field of Search ................................ 623/2.38, 2.39, 623/2.4, 2.12–2.19, 900, 904; 600/37

(56) References Cited

U.S. PATENT DOCUMENTS

| | | |
|---|---|---|
| 3,570,014 | 3/1971 | Hancock . |
| 3,739,402 | 6/1973 | Cooley et al. . |
| 4,035,849 | 7/1977 | Angell et al. . |
| 4,477,930 | 10/1984 | Totten et al. . |
| 4,759,758 | 7/1988 | Gabbay . |
| 5,032,128 | 7/1991 | Alonso . |
| 5,156,621 | 10/1992 | Navia et al. . |
| 5,545,215 * | 8/1996 | Duran ................................. 623/2.1 X |
| 5,584,879 | 12/1996 | Reimold et al. . |

FOREIGN PATENT DOCUMENTS

95/28899 * 11/1995 (WO) ................................. 623/2.19

OTHER PUBLICATIONS

"An Appraisal of the Ross Procedure: Goals & Technical Guidelines", *Operative Techniques in Cardiac & Thoracic Surgery*, vol. 2, No. 4, Nov. 1997; pp. 289–301.

"Modified Pulmonary Autograft Aortic Root Replacement: The Sinus Obliteration Technique", Michael D. Black, MD, Jacques A. M. von Son, MD, PhD & Frank L. Hanley, MD, *The Society of Thoracic Surgeons*, 1995; 60:1434–6.

* cited by examiner

*Primary Examiner*—David H. Willse
(74) *Attorney, Agent, or Firm*—Amin & Turocy, LLP

(57) ABSTRACT

An apparatus and method are disclosed for supporting a heart valve with a flexible girdle. The girdle has an elongated cylindrical sidewall having an axial length at least commensurate with the heart valve. The girdle is disposed around a tubular valve wall of the heart valve being implanted so that the inflow end of the girdle is adjacent the inflow end of the tubular valve wall. The inflow ends of the girdle and heart valve may then be sutured together to implant the valve. The girdle provides support to stabilize the heart valve and inhibit deformation thereof.

44 Claims, 3 Drawing Sheets

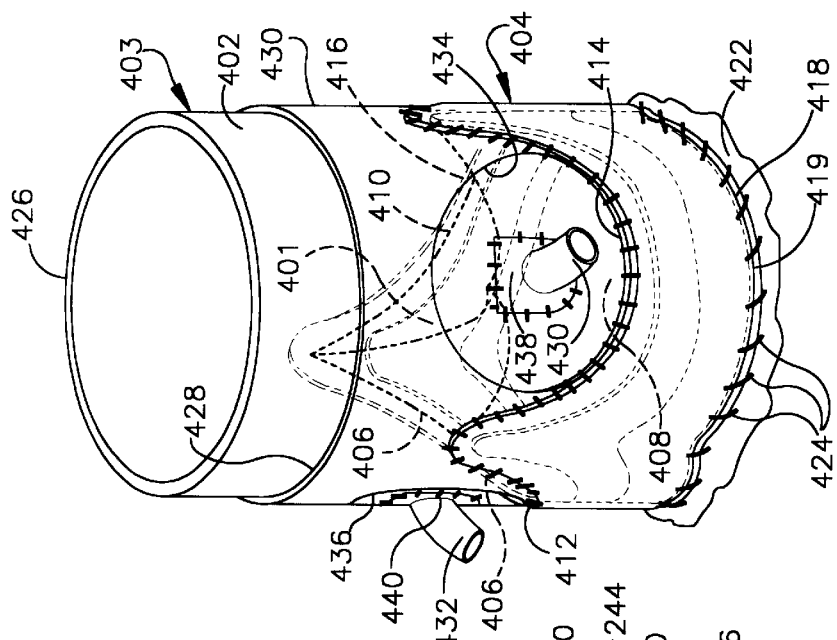
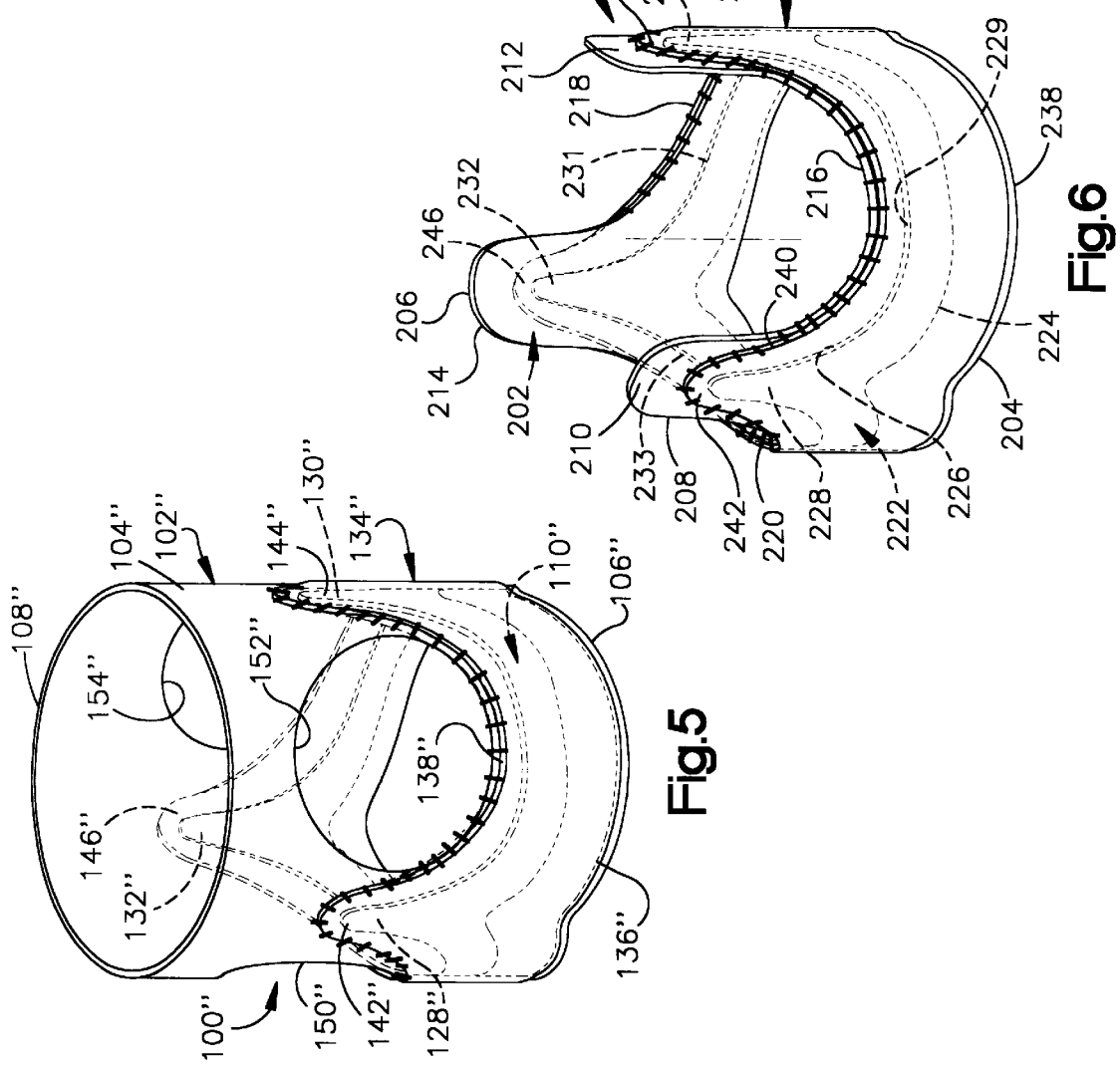

APPARATUS AND METHOD FOR SUPPORTING A HEART VALVE

CROSS REFERENCE TO RELATED APPLICATION

This application is related to U.S. patent application Ser. No. 09/1052,707, now U.S. Pat. No. 5,935,163, which was filed Mar. 31, 1998 and entitled Natural Tissue Heart Valve Prosthesis.

TECHNICAL FIELD

The present invention relates to an apparatus and method for supporting a heart valve. More particularly, the present invention relates to an apparatus and method for supporting a heart valve by disposing a girdle externally about the valve.

BACKGROUND OF THE INVENTION

The use of a patient's healthy pulmonic valve as an autograft to replace a diseased aortic valve has been gaining worldwide acceptance as a viable alternative for replacing the patient's diseased aortic valve. This procedure is known as the Ross procedure after the surgeon who introduced the procedure in 1967.

The Ross procedure is performed by transplanting a patient's healthy pulmonic valve along with a portion of the pulmonary artery to replace the aortic valve and a few centimeters of the aorta. The left and right coronary arteries are attached to the valve wall of the pulmonary autograft after making small slits through the valve wall into coronary sinuses of the autograft.

The pulmonic valve is typically replaced by a homograft, such as a pulmonic or aortic heart valve from a cadaver. The Ross procedure is preferred over other heart valve replacement procedures, especially for individuals who are unable to take anticoagulation drugs. The Ross procedure has received substantial discussion in various publications.

For example, Oury et al., An Appraisal of the Ross Procedure: Goals and Technical Guidelines, Operative Techniques in Cardiac and Thoracic Surgery, Vol. 2, No. 4 (November), 1997: pp. 289–301, describes the Ross procedure as well as some alternative techniques for performing the procedure.

Black et al., Modified Pulnronary Autograft Aortic Root Replacement: The Sinus Obliteration Technique, Ann Thoracic Surgery, 1995; 60:1434–1436, describes a rather complicated technique to remedy a frequent problem of dilation of the pulmonary autograft following the Ross procedure. This approach utilizes large coronary buttons to replace the pulmonary sinus completely and leaves the non-coronary aortic sinus to support the non-coronary sinus of the pulmonary autograft.

SUMMARY OF THE INVENTION

The present invention is directed to an external support apparatus for a heart valve that is disposed within an elongated tubular valve wall. The apparatus includes a girdle having an elongated cylindrical sidewall with inflow and outflow ends that are spaced apart an axial length that is at least substantially commensurate with the axial length of the heart valve disposed within the tubular valve wall.

Preferably, at least two apertures are formed through the sidewall of the girdle and spaced axially from the inflow end thereof. The apertures are spaced circumferentially apart for generally radial alignment with corresponding sinuses of the heart valve which is to be supported by the girdle. The inflow end of the girdle preferably is folded toward the outflow end to provide additional support at its inflow end.

In another embodiment, the girdle, as described above, is further supported by a stent disposed externally about the sidewall of the girdle.

Yet another embodiment of the present invention is directed to a method for improving implantation of a heart valve having inflow and outflow ends and located within a tubular valve wall. An elongated cylindrical girdle is disposed about the tubular valve wall and the heart valve located therein so as to inhibit deformation of the heart valve. The girdle has a cylindrical sidewall portion with inflow and outflow ends spaced apart an axial length at least substantially commensurate with the axial length of the heart valve located within the zubular valve wall. The inflow end of the girdle is positioned adjacent the inflow end of the tubular valve wall. During implantation of the heart valve, the inflow ends of the valve and girdle preferably are secured together to an outflow annulus of the heart.

BRIEF DESCRIPTION OF THE DRAWINGS

The foregoing and other features and advantages of the present invention will become apparent to those skilled in the art to which the present invention relates upon reading the following description with reference to the accompanying drawings, wherein:

FIG. 5 is a fifth embodiment of an apparatus in accordance with the present invention;

FIG. 6 is a sixth embodiment of an apparatus in accordance with the present invention;

FIG. 9 is an isometric view of the apparatus of FIG. 5 disposed about a heart valve in accordance with the present invention.

DESCRIPTION OF PREFERRED EMBODIMENTS

Figure 1:
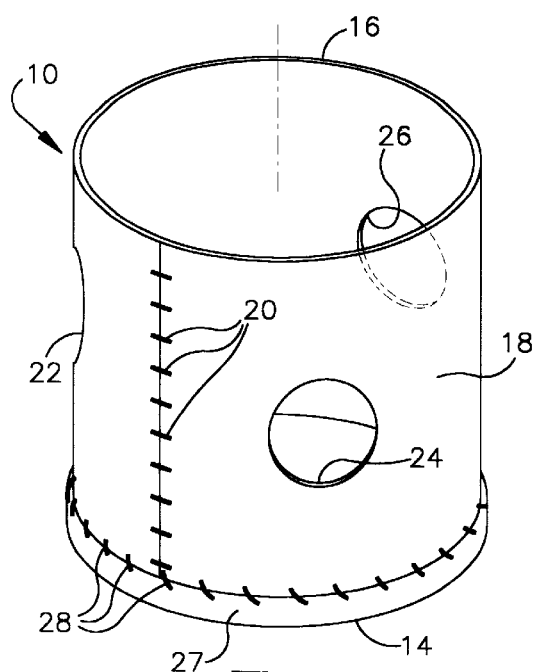
FIG. 1 is a first embodiment of an apparatus in accordance with the present invention.

FIG. 1 illustrates a first embodiment of a heart valve girdle 10 in accordance with the present invention. The girdle 10 has an inflow end 14 and an outflow end 16 spaced apart by a length of a cylindrical sidewall 18. The terms "inflow" and "outflow" are used herein to refer to ends of the girdle which are to be positioned at corresponding ends of a heart valve.

Because the girdle 10 is to be mounted externally about a heart valve, such as an autogenous or homogenous heart valve disposed within a length of a tubular valve wall, the axial length of the sidewall 18 is at least substantially commensurate with the axial length of the heart valve which is to be mounted therein. The girdle 10 also has an inner diameter substantially equal to the outer diameter of the tubular valve wall surrounding the heart valve. The girdle 10 my by provided in a variety of sizes from which a surgeon may select an appropriate size of girdle. The elongated sidewall 18 supports and stabilizes the heart valve from its inflow end to its outflow end, thereby inhibiting deformation of the valve when implanted.

Preferably, the girdle 10 is formed from a sheet of a flexible material. The flexible material may, for example, be a textile material, such as Dacron, or an animal tissue material, such as bovine pericardium, equine pericardium, porcine pericardium, human pericardium, or other biological materials. The girdle 10 alternatively could be formed of a flexible plastic-like material, such as a natural or synthetic polymer, for example, Delrin.

In the preferred embodiment, the girdle 10 is formed from a strip of pericardium which has been treated, or tanned, to render the tissue biocompatible, as is known in the art. The cyLindrical sidewall 18 of the girdle 10 is, for example, formed from a rectangular strip of pericardium having ends that have been attached together end-to-end, such as by sutures 20. The pericardial tissue may be treated before and/or after the girdle 10 has been formed into its tubular configuration. By treating the pericardial tissue material mounted over a right circular, cylindrical mandrel, for example, the girdle 10 is permanently fixed in its desired tubular shape.

At least two and preferably three apertures 22, 24 and 26 are formed through the sidewall 18 of the girdle 10 at an axial location intermediate the first and second ends 14 and 16. In order to facilitate proper alignment of the girdle 10 about the heart valve, each of the apertures 22, 24 and 26 is spaced circumferentially apart for generally radial alignment with a corresponding sinus of the heart valve to be mounted therein. By way of example, a pulmonic autograft, as well as a homograft, such as from a cadaver, has three leaflets with sinuses located at the outflow end of the valve between commissures of each adjacent pair of leaflets. The apertures 22, 24, and 26 of the girdle 10 are spaced circumferentially apart from adjacent apertures, generally about 120° apart, so as to correspond to a location of a respective sinus of the heart valve.

The inflow end 14 of the girdle 10 preferably is folded radially outward and toward the outflow end 16 of the girdle to form an outer folded portion 27. The radially outer folded portion 27 is connected to the radially inner portion of the sidewall 18, such as by sutures 28. This provides two overlapping layers of the sidewall 18 at the inflow end 14 of the girdle 10 to further help stabilize the inflow end of the heart valve. The folded portion 27 also provides an implantation flange to facilitate implantation of the heart valve to an outflow annulus of the heart as well as to inhibit dilation of the heart valve.

Figure 2:
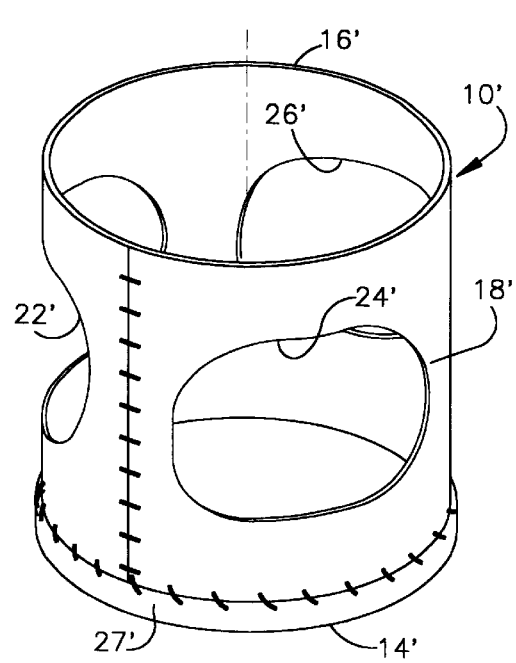
FIG. 2 is a second embodiment of an apparatus in accordance with the present invention.

FIG. 2 illustrates a second embodiment of a girdle 10' in accordance with the present invention in which reference numbers, modified by adding a prime symbol, are used to refer to similar parts of the girdle of FIG. 1. The apertures 22', 24', and 26' are substantially enlarged when compared to the apertures of FIG. 1. Specifically, the circumferential arc of the sidewall 18 extending between adjacent apertures 22', 24' and 26' is substantially less than the circumferential arc of each aperture. In addition, the axial length of sidewall portion 18' between each aperture 22', 24' and 26' and the inflow and outflow ends 14' and 16' also is substantially less than the axial length of each aperture.

The girdle 10' of FIG. 2 advantageously facilitates the positioning of the girdle around the heart valve. This is because two of the large apertures 22', 24', 26' are more easily aligned with coronary sinuses of the heart valve being implanted. Attachment of the coronary arteries to the valve wall of a heart valve mounted within the girdle 101 also is facilitated because of the larger surface area of the valve's sidewall exposed through each aperture 22', 24' and 26'.

Figure 3:
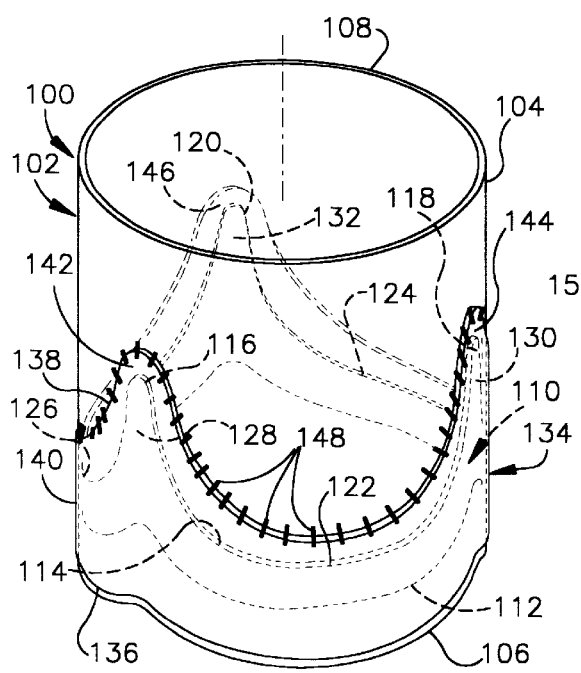
FIG. 3 is a third embodiment of an apparatus in accordance with the present invention.

FIG. 3 is a third embodiment of a girdle 100 in accordance with the present invention. The girdle 100 includes an elongated inner tubular sheath 102 having an elongated cylindrical sidewall 104 which, like the embodiments of FIGS. 1 and 2, has an axial length at least substantially commensurate with the axial length of the heart valve to be mounted therein. The inner sheath 102 has an inflow end 106 and an outflow end 108 spaced apart by the sidewall portion 104.

A stent 110 having an annular inflow end 112 and an outflow end 114 is disposed about the inner sheath 102 intermediate its inflow and outflow ends 106 and 108, respectively. The stent 110 preferably fits snugly over the inner sheath 102. The stent 110 is formed of a flexible material, suitably a resilient metal or a plastic-like material, such as Delrin. Other resilient, flexible materials such as textile materials, pericardial tissue, or other biocompatible materials, also may be used to form the stent 110.

At least the outflow end 114 of the stent 110 is generally sinusoidal with alternating peaks 116, 118, 120 and sinuses 122, 124, 126, respectively. The peaks 116, 118, and 120 are defined by elongated stent posts 128, 130, and 132, which are spaced circumferentially apart. The sinuses 122, 124, and 126 are formed between each adjacent pair of stent posts 128, 130 and 132. The circumferential positioning of the stent posts 128, 130, and 132 corresponds to the circumferential positioning of the commissures of adjacent leaflets of the heart valve.

An outer sheath 134 of a biocompatible material, such as pericardium, a textile material, or any other biocompatible, flexible material, covers the stent 110 and at least a substantial portion of the inner sheath 102. The outer sheath 134 has an inflow end 136 and an outflow end 138 spaced axially apart from the inflow end 136 by a length of cylindrical sidewall 140.

The inflow end 136 of the outer sheath 134 is positioned adjacent the inflow end 106 of the inner sheath 102. The overlapping Layers adjacent the inflow ends 132 and 106 provide additional support at the inflow end of the heart valve, similar to the folded portions 27 and 27' of FIGS. 1 and 2, respectively. A fold also may be added to one or both of the inflow ends 106, 136 to provide further stabilization at the inflow end of the heart valve.

The outflow end 138 of the outer sheath 134 is spaced from the outflow end 114 of the stent 110. Preferably, the outflow end 138 of the outer sheath 134 is contoured according to the outflow end 114 of the stent 110. That is, it has elongated flanges 142, 144 and 146, which cover each of the respective stent posts 128, 130, and 132. Sinuses are formed between adjacent pairs of flanges 142, 144, 146. The outflow end 138 of the outer sheath 134 is connected to the sidewall 104 of the inner sheath 102, such as by sutures 148. The sutures 148 limit or prevent axial movement of the stent 110 in a direction from the inflow end 106 toward the outflow end 108 of the inner sheath 102.

The sidewall portions 104 and 140 alternatively could be coextensive, with the outflow end 138 of the outer sheath 134 connected to the outflow end 108 of the inner sheath 102. In addition, the inflow ends 106 and 136 and may be connected together by sutures (See FIG. 8) when the heart valve is implanted to an appropriate outflow annulus of a patient's heart. This maintains the axial as well as angular positioning of the stent 110 between the inflow and outflow ends 136 and 138 of the outer sheath 134.

Figure 4:
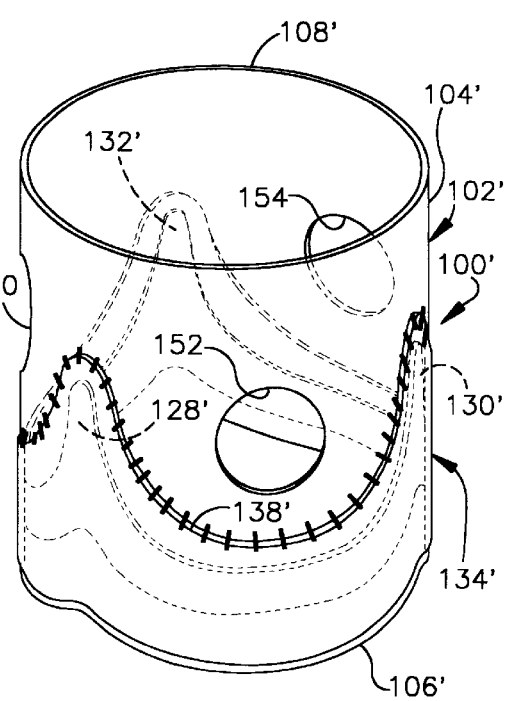
FIG. 4 is a fourth embodiment of an apparatus in accordance with the present invention.

FIG. 4 is another embodiment of a girdle 100', in accordance with the present invention, in which a prime symbol (') has been added to the reference numbers of FIG. 3 to indicate corresponding parts. The girdle 100' is substantially identical to the girdle 100 of FIG. 3. However, a plurality of apertures 150, 152 and 154 are formed through the sidewall 104' of the inner sheath 102'.

The apertures 150, 152, and 154 are substantially identical to the apertures 22, 24 and 26 shown and described with respect to FIG. 1. The apertures 150, 152, and 154 are spaced axially apart from the inflow and outflow ends 106' and 108'. The apertures 150, 152, and 154 also are spaced axially from the sinusoidal outflow end 138' of the outer sheath 134'. In addition, the apertures 150, 152, and 154 are spaced circumferentially apart and located intermediate adjacent stent posts 128', 130' and 132' for generally radial alignment with corresponding sinuses of a heart valve to be mounted therein. The apertures 150, 152, and 154 provide access to the sinuses of the heart valve, such as a pulmonary autograft, to facilitate connecting the left and right coronary arteries through the apertures and to the valve wall surrounding the heart valve.

FIG. 5 is another embodiment of a girdle 100" in accordance with the present invention in which a double prime symbol (") has been added to reference numbers of FIGS. 3 and 4 to indicate corresponding parts. The girdle 100" is substantially identical to the girdle 100' of FIG. 4, although the apertures 150", 152", and 154" have been enlarged to facilitate alignment of two of the apertures 150", 152", and 154" with coronary sinuses of the heart valve to be mounted therein. Specifically, the outer sheath 134" has a sinusoidal outflow end 138" with elongated flanges 142", 144" and 146" radially aligned with and covering respective stent posts 128", 130" and 132". Sinuses are formed between adjacent flanges 142", 144", 146". The apertures 150", 152", and 154" are formed through the inner sheath 102" coextensively with each such sinus of the outer sheath 134". The circumferential arc of the sidewall portion 104" extending between adjacent apertures 150", 152" and 154", e.g. the circumferential arc length of flanges 142", 144" and 146", is substantially less than the circumferential arc of each aperture.

FIG. 6 illustrates yet another embodiment of a girdle 200 in accordance with the present invention. The girdle 200 is generally similar to the girdles 100, 100', and 100" of FIGS. 3–5. The girdle 200 includes an elongated inner sheath 202 having an inflow end 204 and an outflow end 206 spaced axially apart by a cylindrical sidewall portion 208.

In this embodiment, the outflow end 206 of the inner sheath 202 is sinusoidal to correspond to the contour of the outflow end of a heart valve to be mounted therein. Specifically, the outflow end 206 includes a plurality of elongated flanges 210, 212, and 214 which are spaced circumferentially apart. In this way, sinuses 216, 218, and 220 are formed in the outflow end 206 between each adjacent pair of flanges 210, 212, and 214.

A flexible stent or annular ring 222, which is substantially identical to that shown and described with respect to FIGS. 3–5, is disposed about the inner sheath 202 to provide additional radial support. The stent 222 includes axially spaced apart inflow and outflow ends 224 and 226. The outflow end 226 is sinusoidal with circumferentially spaced apart and elongated stent posts 228, 230, and 232 extending axially from the annular portion at inflow end 224. Each stent post 228, 230, and 232 is radially aligned and extends substantially coextensively with one of the respective flanges 210, 212, and 214, as shown in FIG. 6. The stent 222 also has sinuses 229, 231 and 233 formed between adjacent pairs of stent posts 228, 230 and 232. The inflow and outflow ends 224 and 226 of the stent 222 are spaced axially apart from the respective inflow and outflow ends 204 and 206 of the inner sheath 202 to form a generally cylindrical sidewall portion therebetween.

An outer sheath 236 of a flexible material, such as a textile or animal tissue material, is disposed externally over the stent 222 and at least a portion of the inner sheath 202. The outer sheath 236 has an inflow end 238 adjacent the inflow end 204 of the inner sheath 202 and an outflow end 240 adjacent the outflow end 206 of the inner sheath. Preferably, the outflow end 240 of the outer sheath 236 also is sinusoidal with corresponding elongated peaks or flanges 242, 244, and 246 radially aligned and substantially coextensive with the respective flanges 210, 212, and 214 of the inner sheath 202 and the stent posts 228, 230, and 232. The outflow end 240 also has sinuses at its outflow end intermediate adjacent pairs of the elongated peaks 242, 244, and 246, which outer sheath sinuses are aligned with the inner sheath sinuses 216, 218, and 220. The outer sheath 236 alternatively may have an axial length about equal with axial length of the inner sheath 202, so that the stent 222 is sandwiched between concentric inner and outer cylindrical sheaths.

Figure 8:
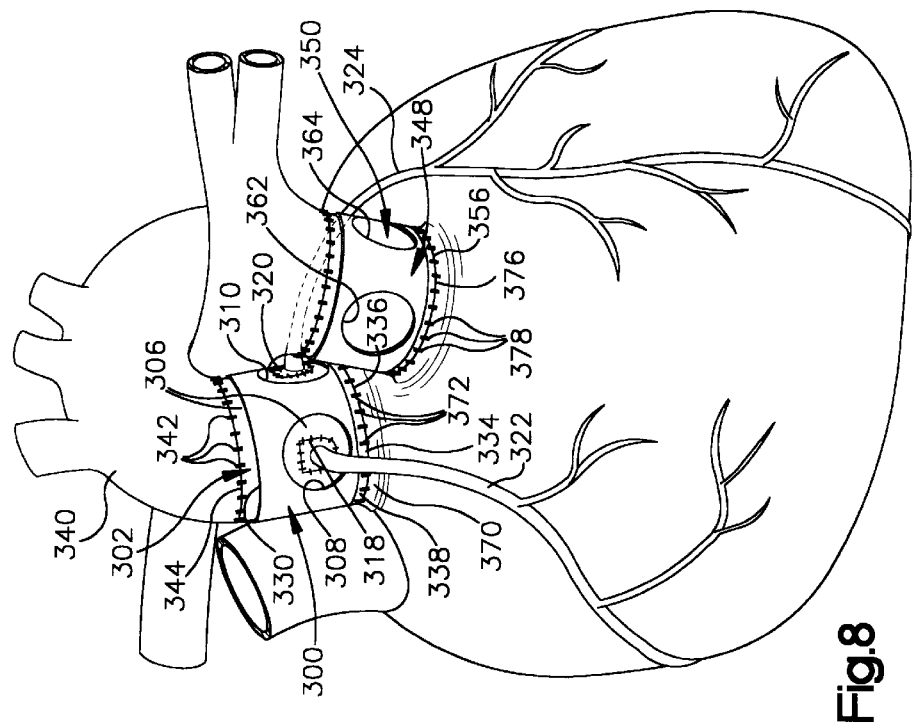
FIG. 8 is an isometric view, similar to FIG. 7, illustrating a completed heart valve transplant procedure using the apparatus of FIG. 1.
Figure 7:
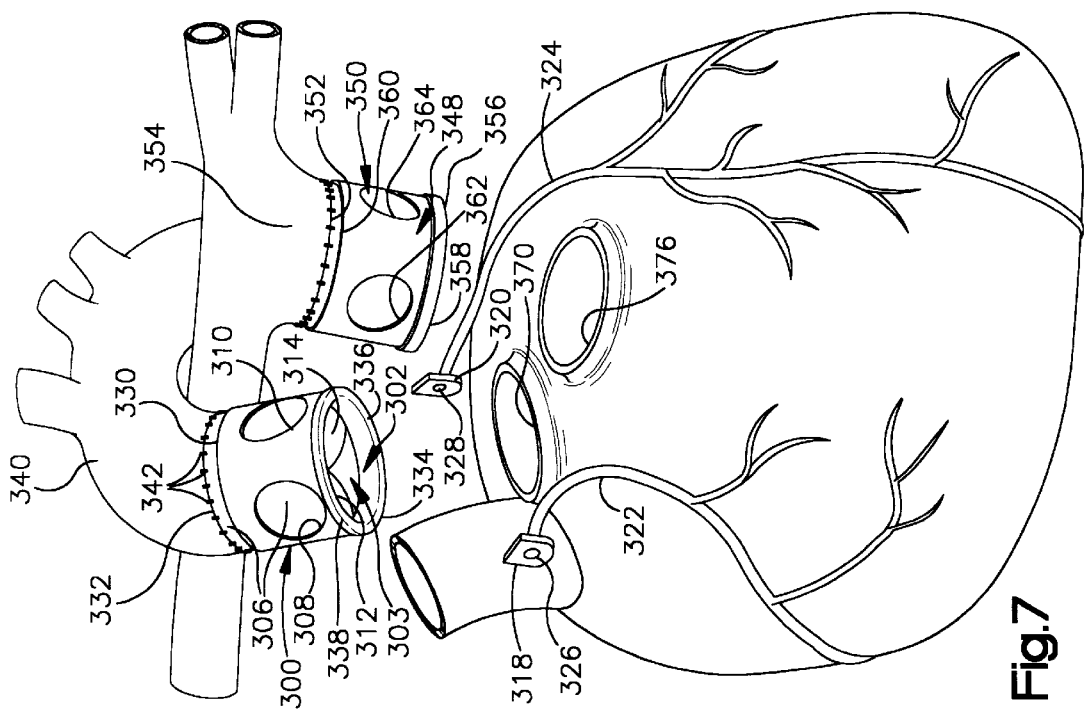
FIG. 7 is an is ometric view of the apparatus of FIG. 1 mounted to a heart valve being implanted to a patient's heart.

In view of the various embodiments of girdles described above, their use may be better appreciated with reference to FIGS. 7–9. While FIGS. 7–9 disclose the use of two particular girdle embodiments, it will be understood and appreciated that each of the girdle embodiments shown in FIGS. 1–6 may, in accordance with the present invention, be used to support a heart valve being implanted.

FIG. 7 illustrates part of a surgical procedure in which a girdle 300, as shown in FIG. 1, has been attached about an autogenous heart valve, preferably a pulmonary autograft 302. The procedure preferably follows the steps of the Ross procedure, such as described in Oury et al., An Appraisal of the Ross Procedure: Goals and Technical Guidelines, Operative Techniques in Cardiac and Thoracic Surgery, Vol. 2, No. 4 (November), 1997: pp. 289–301, which is incorporated herein by reference.

In FIG. 7, the Ross procedure is at an intermediate stage in which the diseased aortic valve already has been removed and discarded. A pulmonary autograft 302 is formed of a healthy pulmonary heart valve 303 which is disposed within an elongated portion of the tubular valve wall or pulmonary artery 306. The portion of the pulmonary artery 306 enclosing the heart valve 303 has been excised from the pulmonary trunk of the patient.

The external support girdle 300, in accordance with the present invention, is disposed about the pulmonary autograft valve 302. The girdle 300 has apertures 308 and 310 which are radially and axially aligned with the sinuses of coronary leaflets 312 and 314 of the pulmonary autograft 302.

During the Ross procedure, small incisions or slits are made in the tubular valve wall 306 of the pulmonary autograft 302 over which buttons 318 and 320 are attached. The buttons 318 and 320 are formed of sidewall portions of the aortic valve wall from the patient's aortic valve which has been removed. The buttons 318 and 320 are connected with the right and left coronary arteries 322 and 324, respectively. The right and left coronary arteries 322 and 324 terminate at the buttons 318 and 320 to form ostias or openings 326 and 328 which are subsequently aligned with slits formed in the valve wall 306 of the pulmonary autograft 302.

As shown in FIG. 7, the girdle 300 has an outflow end 330 located adjacent but spaced apart from an outflow end 332 of the pulmonary valve wall 306. An inflow end 334 of the girdle 300 is located adjacent an inflow end 336 of the pulmonary valve wall 306 and includes a fold 338, as described above, to help inhibit dilation at the inflow end 336 of the pulmonary autograft 302. The outflow end 332 of the pulmonary valve wall 306 is anastomosed to the aorta 340, such as by sutures 342.

Another girdle 348, in accordance with the present invention, is mounted over a homograft heart valve 350. The homograft 350 has an outflow end 352 which has been anastomosed to the pulmonary trunk 354. An inflow end 356 of the girdle 348 is positioned adjacent the inflow end 358 of the homograft 350. An outflow end 360 of the girdle 348 preferably is spaced from the outflow end 352 of the homograft 350, although it easily could be made longer so that the girdle 348 and homograft 350 are coextensive.

While the girdle 348 is shown to include apertures 362 and 364, such apertures are superfluous for the pulmonary valve replacement. However, manufacturing costs may be reduced by fabricating a single type of girdle 300, 348 for use during the Ross procedure. The girdles 300, 348 typically are produced in various sizes which are to be selected by the surgeon performing the procedure.

FIG. 8 illustrates the completed procedure in which the inflow end 336 of the pulmonary autograft 302 and the inflow end 334 of the girdle 300 have been connected together and anastomosed to the right ventricle outflow tract 370, suitably by interrupted or continuous sutures 372. In addition, the right and left coronary artery buttons 318 and 320 have been connected over appropriate slits (not shown) formed in the pulmonary valve wall 306 through the apertures 308 and 310, thereby connecting the coronary arteries with coronary sinuses of the autograft 302. The inflow end 356 of the girdle 348 and the inflow end of the pulmonary homograft 350 also are connected together and are anastomosed to the left ventricle outflow tract 376 by sutures 378.

FIG. 9 illustrates a heart valve, such as a pulmonary valve 401 disposed within its outer tubular valve wall 402 define a pulmonary autograft 403. The autograft 403 is mounted within a girdle 404, such as the girdle shown in FIG. 5. As can be seen, each sinus 406, 408, and 410 formed in the outflow end of the valve 401 is aligned with a corresponding sinus 412, 414 and 416 of the girdle 404. An inflow end 418 of the girdle 404 is positioned ad.,acent the inflow end 419 of the valve wall 402. The inflow ends 418 and 419 are connected together and anastomosed to an outflow annulus, schematically indicated at 422, by sutures 424. An outflow end 426 of the pulmonary valve wall 402 extends axially beyond an outflow end 428 of the tubular inner sheath 430 of the girdle 404. The outflow end 426 of the valve wall 402 will be anastomosed to the aorta (not shown) in a manner known in the art.

Left and right coronary arteries 430 and 432 are attached to the valve wall 402 through respective apertures 434 and 436 of the girdle 404. In particular, the coronary arteries 430 and 432 terminate in buttons 438 and 440 which are anastomosed to the valve wall 402 over slits or apertures (not shown) that have been formed through the valve wall. Such slits provide access into coronary sinuses 408 and 406 of the valve 401.

Advantageously, a girdle, in accordance with the present invention, stabilizes the base of the heart valve and supports the commissures so as to inhibit their inward deflection. The girdle also increases the durability of the autograft and homograft valve by inhibiting annular dilation and/or deformities which might otherwise occur during normal functioning of the heart. Such deformities often lead to malcoaptation which, in turn, tends to cause insufficiency and failure. The girdles advantageously promote coaptation of the leaflets of the autograft and homograft. This, in turn, reduces the likelihood of failure and the need for reoperation after surgical procedures, such as the Ross procedure.

Each of the girdles of FIGS. 1–6 also may be formed entirely of an absorbable synthetic or biological material, such as an absorbable textile material or an absorbable treated animal tissue material, for example, pericardium. The absorbable material girdle is especially advantageous for young patient's undergoing the Ross procedure. Because the autograft is formed of the patient's own tissue, for relatively young individuals, the autograft will continue to grow after being implanted. As stated above, the absorbable girdle stabilizes the transplanted pulmonary autograft for an extended period of time. The absorbable girdle, by its very nature, is slowly absorbed. This permits the transplanted autograft, including the heart valve and corresponding tubular valve wall, to grow with the patient.

From the above description of the invention, those skilled in the art will perceive improvements, changes and modifications. Such improvements, changes and modifications within the skill of the art are intended to be covered by the appended claims.

Having described the invention, the following is claimed:

1. A external support apparatus for supporting a heart valve disposed within an elongated tubular valve wall, the apparatus comprising:

a girdle having an elongated sidewall with inflow and outflow ends spaced apart an axial length at least subtantially commensurate with axial length of the valve leaflets of the heart valve;

a stent disposed about the sidewall of the girdle intermediate the inflow and outflow ends of the sidewall of the girdle; and a sheath of biocompatible material covering the stent and at least a portion of the girdle, the sheath having an inflow edge adjacent the inflow end of the sidewall of the girdle, the sheath having an outflow edge spaced axially beyond an outflow end of the stent.

2. An apparatus as set forth in claim 1 wherein a sinus is defined by each valve leaflet at an outflow end of the heart valve, said girdle further including at least two apertures extending through said sidewall of said girdle spaced axially from the inflow end of said girdle, each of said apertures being spaced circumferentially apart for generally radial alignment with a corresponding one of the sinuses of the heart valve.

3. An apparatus as set forth in claim 1 wherein a portion of said sidewall of said girdle adjacent said inflow end is folded toward the outflow end of said girdle and connected to said sidewall of said girdle, whereby the folded portion may be connected at an inflow end of the heart valve to inhibit dilation of the heart valve.

4. An apparatus as set forth in claim 3 wherein a sinus is defined by each valve leaflet at an outflow end of the heart valve, said girdle further including at least two apertures extending through said sidewall of said girdle spaced axially from the inflow end of said girdle, each of said apertures being spaced circumferentially apart for generally radial alignment with a corresponding one of the sinuses of the heart valve.

5. An apparatus as set forth in claim 1 wherein the outflow edge of said sheath is connected to said sidewall of said girdle intermediate the outflow end of said stent and the outflow end of said girdle.

6. An apparatus as set forth in claim 1 wherein said sheath is formed of an animal tissue material.

7. An apparatus as set forth in claim 1 wherein said sheath is formed of a textile material.

8. An apparatus as set forth in claim 1 wherein the outflow end of said girdle has a plurality of lobes which extend axially beyond said outflow end of said stent so as to extend beyond an outflow end of the heart valve.

9. An apparatus as set forth in claim 1 wherein said girdle is formed of an animal tissue material.

10. An apparatus as set forth in claim 1 wherein said girdle is formed of a textile material.

11. An apparatus as set forth in claim 1 wherein said girdle is formed of a plastic-like material.

12. An apparatus as set forth in claim 1 wherein said girdle is formed of an absorbable material so as to permit growth of the heart valve after being implanted.

13. An external support apparatus for a heart valve disposed within a tubular valve wall, the heart valve extending an axial length within the tubular valve wall, the apparatus comprising:

an elongated cylindrical inner sheath of a biocompatible material having spaced apart inflow and outflow edges; and a flexible stent disposed externally about the inner sheath, the stent having inflow and outflow ends spaced respectively from and intermediate the inflow and outflow edges of the inner sheath, the inner sheath having an outflow portion that extends beyond the outflow end of the stent a length sufficient to extend beyond an outflow end of the heart valve.

14. An apparatus as set forth in claim 13 further including an outer sheath of natural tissue covering said stent and at least a portion of said inner sheath, said outer sheath having an inflow end adjacent the inflow edge of said inner sheath, said outer sheath having an outflow end spaced axially from the outflow end of said stent.

15. An apparatus as set forth in claim 14 wherein the outflow end of said outer sheath is connected to said inner sheath intermediate the outflow end of said stent and the outflow edge of said inner sheath.

16. An apparatus as set forth in claim 14 wherein said outer sheath is formed of a textile material.

17. An apparatus as set forth in claim 14 wherein said outer sheath is formed of a biological material.

18. An apparatus as set forth in claim 13 wherein said stent has a sinusoidal outflow end with alternating peaks and sinuses corresponding to the contour of the outflow end of the heart valve.

19. An apparatus as set forth in claim 18 wherein each peak of said stent is defined by a stent post, each of said stent posts being circumferentially spaced apart so as to align with commissures of adjacent leaflets of the heart valve.

20. An apparatus as set forth in claim 13 wherein said inner sheath is formed of a biological material.

21. An apparatus as set forth in claim 13 wherein said inner sheath is formed of a textile material.

22. An apparatus as set forth in claim 13 wherein said inner sheath is formed of a plastic-like material.

23. An apparatus as set forth in claim 13 wherein the outflow portion of said inner sheath has a plurality of lobes which extend axially beyond the outflow end of said stent.

24. An apparatus as set forth in claim 13 wherein the outflow portion further comprises a substantially tubular portion which extends beyond the outflow end of the stent an axial length sufficient to extend beyond the outflow end of the heart valve.

25. An apparatus as set forth in claim 24 wherein at least two apertures are formed though the tubular portion of said inner sheath, each of said apertures being spaced circumferentially apart for generally radial alignment with a corresponding sinus of the heart valve.

26. An apparatus as set forth in claim 13 wherein said inner sheath and stent are each formed of an absorbable material, whereby the growth of the heart valve is permitted after being implanted.

27. An external support apparatus for a heart valve disposed within a tubular valve wall, the heart valve extending an axial length within the tubular valve wall, the apparatus comprising:

an elongated cylindrical inner sheath of a flexible material aving spaced apart inflow and outflow ends; and a flexible stent disposed externally about the inner sheath, the stent having inflow and outflow ends spaced respectively from the inflow and outflow ends of the inner sheath so that at least a substantial length of the outflow end of the inner sheath extends beyond the outflow end of the stent;

wherein the outflow end of the inner sheath has a generally tubular portion that extends beyond the outflow end of the stent, the tubular portion of the inner sheath having an axial length sufficient to extend beyond an outflow end of the heart valve, at least two apertures being formed through the tubular portion of the inner sheath, each of the apertures being spaced circumferentially apart for generally radial alignment with a corresponding sinus of the heart valve.

28. A method for implanting an autogenous or homogenous heart valve disposed within a length of a tubular valve wall having first and second ends, the heart valve having inflow and outflow ends spaced axially from the respective first and second ends of the tubular valve wall, said method comprising the steps of:

providing the heart valve disposed within the tubular valve wall;

disposing an elongated girdle externally about the tubular valve wall at least substantially coextensive with the heart valve to support the heart valve and inhibit deformation thereof, the girdle having a cylindrical sidewall with inflow and outflow ends spaced apart an axial length at least substantially commensurate with the axial length of the heart valve disposed within the tubular valve wall, the inflow end of the girdle being adjacent the first end of the tubular valve wall, the girdle having a generally tubular portion at the outflow end thereof having an axial length sufficient to extend beyond the outflow end of the heart valve.

29. A method as set forth in claim 28 wherein, prior to said step of disposing, at least two apertures are formed through the sidewall of the girdle at a location spaced axially from the inflow end of the girdle, each of the apertures being spaced apart circumferentially for substantially radial alignment with a corresponding sinus of the heart valve.

30. A method as set forth in claim 28 further including the step of forming at least two circumferentially spaced apart apertures through the sidewall of the girdle, each aperture being radially aligned with a sinus of the heart valve.

31. A method as set forth in claim 28 wherein said step of providing further includes removing the heart valve from a patient to define an autogeneous heart valve.

32. A method as set forth in claim 31 wherein after said step of disposing, the method further includes the step of implanting the supported heart valve in the patient from which it had been removed.

33. A method as set forth in claim 32 wherein said step of implanting includes connecting both the inflow end of the girdle and the first end of the tubular valve wall portion to an annulus of the patient's heart, whereby the implanted heart valve is supported by the girdle.

34. A method as set forth in claim 28 wherein the girdle is formed of a textile material.

35. A method as set forth in claim 28 wherein the girdle is formed of an animal tissue material.

36. A method as set forth in claim 28 wherein the girdle is formed of a plastic-like material.

37. A method as set forth in claim 28 wherein the inflow end of the girdle is folded toward the outflow end of the girdle and connected to the sidewall of the girdle so as to provide at least two overlapping layers of the girdle sidewall at the inflow end of the girdle.

38. A method as set forth in claim 28 wherein the girdle further includes a stent disposed about the sidewall of the girdle intermediate the inflow and outflow ends of the girdle.

39. A method as set forth in claim 38 wherein the stent and at least a portion of the sidewall of the girdle are covered with a sheath of flexible biocompatible material, the sheath having an inflow end adjacent the inflow end of the girdle, the sheath having an outflow end connected with the sidewall of the girdle intermediate an outflow end of the stent and the outflow end of the sidewall of the girdle.

40. A method as set forth in claim 39 wherein the tubular outflow portion of the girdle has a plurality of circumferentially spaced apart lobes extending beyond the outflow end of the heart valve proximal the second end of the tubular valve wall.

41. A method as set forth in claim 28 wherein the girdle is formed of an absorbable material so as to permit growth of the heart valve and tubular valve wall after being implanted.

42. An external support apparatus for supporting a heart valve disposed within an elongated tubular valve wall, the apparatus comprising:

a girdle having an elongated sidewall with inflow and outflow ends space apart an axial length at least substantially commensurate with the axial length of valve leaflets of the heart valve, wherein the outflow end of the girdle has a plurality of circumferentially spaced apart lobes that extend axially therefrom a length sufficient to extend beyond an outflow end of the heart valve.

43. The apparatus of claim 42 further comprising a stent disposed about the sidewall of the girdle intermediate the inflow and outflow ends of the sidewall of the girdle.

44. The apparatus of claim 43 further comprising a sheath of biocompatible material covering the stent and at least a portion of the girdle, the sheath having an inflow end adjacent the inflow end of the sidewall of the girdle, the sheath having an outflow end spaced axially from an outflow end of the stent, the plurality of lobes extending axially beyond the outflow end of the sheath.

* * * * *

UNITED STATES PATENT AND TRADEMARK OFFICE
CERTIFICATE OF CORRECTION

PATENT NO.   : 6,264,691 B1
DATED        : July 24, 2001
INVENTOR(S)  : Shlomo Gabbay Page 1 of 1

It is certified that error appears in the above-identified patent and that said Letters Patent is hereby corrected as shown below:

Claim 33,
Line 3, delete "portion".

Signed and Sealed this

Fourth Day of December, 2001

Attest:

NICHOLAS P. GODICI
*Attesting Officer*   *Acting Director of the United States Patent and Trademark Office*